(12) United States Patent
Makioka et al.

(10) Patent No.: US 7,829,044 B2
(45) Date of Patent: Nov. 9, 2010

(54) PHOSPHONAMIDES, PROCESS FOR PRODUCING THE SAME, AND USE THEREOF

(75) Inventors: Yoshikazu Makioka, Ibaraki (JP); Teruyuki Hayashi, Chiba (JP); Masato Tanaka, Ibaraki (JP); Li-Biao Han, Ibaraki (JP)

(73) Assignee: Japan Science and Technology Agency, Saitama (JP)

( * ) Notice: Subject to any disclaimer, the term of this patent is extended or adjusted under 35 U.S.C. 154(b) by 997 days.

(21) Appl. No.: 10/506,424

(22) PCT Filed: Mar. 3, 2003

(86) PCT No.: PCT/JP03/02422

§ 371 (c)(1),
(2), (4) Date: Sep. 2, 2004

(87) PCT Pub. No.: WO03/074538

PCT Pub. Date: Sep. 12, 2003

(65) Prior Publication Data

US 2005/0107599 A1      May 19, 2005

(30) Foreign Application Priority Data

Mar. 4, 2002    (JP)    ............... 2002-057419

(51) Int. Cl.
C01F 17/00    (2006.01)
C07D 233/02    (2006.01)

(52) U.S. Cl. ..................................... 423/21.5; 548/100

(58) Field of Classification Search ................ 423/21.5; 548/100
See application file for complete search history.

(56) References Cited

U.S. PATENT DOCUMENTS

| 5,186,733 | A | | 2/1993 | Broadhurst et al. |
| 5,232,895 | A | | 8/1993 | Broadhurst et al. |
| 5,708,958 | A | * | 1/1998 | Koma et al. .................... 423/8 |
| 6,258,333 | B1 | * | 7/2001 | Romanovskiy et al. ....... 423/10 |

FOREIGN PATENT DOCUMENTS

| EP | 0 116 483 A | 8/1984 |
| FR | 2 669 348 A | 5/1992 |

OTHER PUBLICATIONS

Abstract of Abdel-Mohdy et al., Book of Papers—International Conference & Exhibition, AATCC (1999) 85-94. (CAPLUS Accession # 2000:743424).*
Delangle et al. (J. Org. Chem, 1996, v. 61, p. 8904-14).*
Alberts et al. (J. Am. Chem. Soc., 1979, v. 101, p. 3545-53).*
Laskorin et al., CAPLUS Abstract of Radiokhimiya (1976), 18(3), 403-6, "Effect of structure on the extraction capacity of phosphorus acid amides."*
Laskorin et al., CAPLUS Abstract of Radiokhimiya (1984), 26(2), 161-6, "Quantitative relations between structure, electron donor capacity, and extraction capacity of heteroorganic compounds."*
Berkova et al., CAPLUS Abstract of Zhurnal Obshchei Khimii (1977), 47(6), 1431-2, "Contact contribution to proton and phosphorus-31 lanthanide shifts in NMR spectra of Phosphonates."*
De Bolster, et al., CAPLUS Abstract of Recueil des Travaux Chimiques des Pays-Bas (1971), 90(11), 1153-65, "Coordination chemistry of phenylbisdimethylaminophosphine oxide."*
CAPLUS Abstract of Laskorin et al., Radiokhimiya (1984), 26(2), 161-6.*
Fadeeva et al. (CAPLUS Abstract of: Zhurnal Neorganicheskoi Khimii (1972), 17(3), 771-5).*
Nash, The Minerals, Metals, and Materials Society (TMS) Annual Meeting, Nashville, TN (US), Mar. 12, 2000-Mar. 16, 2000 ; PBD: Jan. 12, 2000.*
Vodolazov and Shatalov, Atomic Energy, vol. 90, No. 3, 2001.*
de Bolster et al. (Societe chimique neerlandaise Leyde, 1971, 90(11), 1153-65).*
International Search Report Dated Jul. 8, 2003.
Duddeck et al., "Synthesis and Mass Spectra of Adamantylphosphoryl Derivatives," Phosphorus and Sulfur, vol. 28, pp. 307-314, Gordon and Breach, Science Publishers Inc. (1986).

(Continued)

*Primary Examiner*—Robert Havlin
(74) *Attorney, Agent, or Firm*—Westerman, Hattori, Daniels & Adrian, LLP

(57) ABSTRACT

The invention provides a process by which rare earth metal ions can be efficiently extracted by easy operation, and effective extracting reagents for the process. Specifically, phosphonamides represented by the general formula [1]; a process for producing the same; reagents for extracting rare earth metal ions, containing the phosphonamides; and a process for extraction of rare earth metal ions with the phosphonamides: [1] wherein $R^1$ is alkyl, cycloalkyl, alkenyl, cycloalkenyl, alkynyl, aryl, aralkyl, or a heterocyclic group, with the proviso that each group may be substituted; $R^2$ is hydrogen, alkyl, cycloalkyl, alkenyl, cycloalkenyl, aryl, aralkyl, or a heterocyclic group, with the proviso that each group may be substituted; $R^3$ is hydrogen, alkyl, cycloalkyl, alkenyl, cycloalkenyl, aryl, aralkyl, or a heterocyclic group, with the proviso that each group may be substituted, or the two $R^3$s may be united to form alkylene, cycloalkylene, or arylene.

[1]

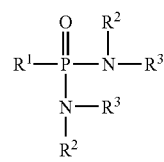

11 Claims, No Drawings

OTHER PUBLICATIONS

Quast et al., "Three-membered Hetrocycles, 10.—Phosphonohydrazidic Esters by Alkoxide-induced Rearrangement of N-Chlorophosphonic Diamides," Liebigs Ann. Chem., No. 5, pp. 943-966 Verlag Chemie GmbH (1981).

Patois et al., "Phosphate-Phosphonate Conversion: Nucleophilic Displacement Reactions Involving Phosphoric Amides and Alkyllithiums," Heteroatom Chemistry, vol. 1, No. 5, pp. 369-374, VCH Publishers, Inc. (1990).

Collins et al., "Organophosphorus Compounds. XX Approaches to the Synthesis of 2,3-Dihydro-1H-1,2-benzazaphospholes Involving C-C and C-P Ring Closure," Aust. J. Chem., vol. 37, pp. 1009-1021 (1984).

Fadeeva et al., "Extraction of Zirconium and Scandium by a Mixture of Benzoylacetone and the Tetraethyldiamide of Heptyl Hydrogen Phosphate," Russian Journal of Inorganic Chemistry, vol. 17, No. 3, pp. 404-406 (1972).

Supplementary European Search Report, Aug. 22, 2006.

Database WPI, Section Ch, Week 197125, Derwent Publications Ltd., London GB; AN 1971-42891S XP002394253 & SU 276 948 A (Moscow MV Lomonosuv Unive), Jul. 22, 1970.

English Translation of the International Preliminary Examination Report, (Sep. 30, 2004).

Supplementary European Search Report, Aug. 22, 2006.

Database WPI, Section Ch, Week 197125, Derwent Publications Ltd., London GB; Class C01, AN 1971-42891S XP002394253 & SU 276 948 A (Moscow MV Lomonosuv Unive), Jul. 22, 1970.

* cited by examiner

PHOSPHONAMIDES, PROCESS FOR PRODUCING THE SAME, AND USE THEREOF

TECHNICAL FIELD

The present invention relates to a novel phosphonamide compound which is useful as an agent for extracting a rare earth metal ion or the like, a process for producing the same and a process for extracting a rare earth metal ion from an aqueous solution containing a rare earth metal ion using the said compound.

BACKGROUND ART

Rare earth elements (a generic name of scandium, yttrium and 15 kinds of lanthanide elements) are used in large quantities as a constitutive element of important materials such as a magnet, an abrasive for hard disk, a hydrogen secondary battery, a catalyst for exhaust gas treatment, an MRI imaging agent and the like. These elements are separated and recovered from the above-mentioned materials as well as separated and purified from monazite, bastnaesite or zenotime which is a mineral ore.

As conventional separation processes of a rare earth element, (1) an ion exchange process, (2) a precipitation process and (3) a solvent extraction process are known. Among them, because the solvent extraction process of (3) enables a continuous separation of large quantities of a rare earth element, it can be considered as the most effective separation process among them.

In the above-mentioned solvent extraction process, by contacting an aqueous solution containing a rare earth element with an extraction agent or an aqueous solution containing an extraction agent and transferring the element from an aqueous layer to an organic layer, the rare earth element can be separated. As the extraction agent, acidic compounds such as dialkylphosphonic acids and carboxylic acids described in p. 251 of "Rare Metal Jiten" (edited by Masao Douyama, issued by Fujitec Corporation, 1991), and neutral compounds such as phosphate esters described in p. 21 of "Kidoruigenso No Kagaku" (written by N. E. Topp, translated by Jiro Shiokawa and Ginya Adachi, issued by Kagaku-Dojin Publishing Co. Inc., 1974) are generally widely known to the public and utilized.

However, by being contacted with an aqueous solution containing a rare earth element, the above-mentioned acidic compounds release hydrogen ions into the aqueous solution and significantly change the characteristics of the aqueous solution, particularly the concentration of hydrogen ions in the aqueous solution. This comprises a problem in that the transfer efficiency of a rare earth element from an aqueous layer to an organic layer is significantly lowered.

On the other hand, the above-mentioned neutral compounds known to date comprises a problem in that the transfer efficiency of a rare earth element from an aqueous layer to an organic layer is intrinsically low.

DISCLOSURE OF THE INVENTION

The present invention aims to provide a process for extracting a rare earth metal ion by which a rare earth metal ion can be efficiently extracted by an easy operation, and an effective extraction agent for the process.

The present inventors have intensively studied in order to solve the above-mentioned problems. As a result, they have found that a phosphonamide compound having a specific structure can be extremely effectively used as an agent for extracting a rare earth metal ion. The present invention has been thus accomplished.

Namely, the present invention relates to a phosphonamide compound represented by the general formula [1]

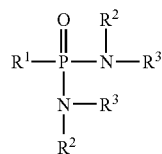

(wherein $R^1$ represents an alkyl group, a cycloalkyl group, an alkenyl group, a cycloalkenyl group, an alkynyl group, an aryl group, an aralkyl group, or a heterocyclic group, with the proviso that each group may have a substituent; $R^2$ represents a hydrogen atom, an alkyl group, a cycloalkyl group, an alkenyl group, a cycloalkenyl group, an aryl group, an aralkyl group, or a heterocyclic group, with the proviso that each group may have a substituent; and $R^3$ represents a hydrogen atom, an alkyl group, a cycloalkyl group, an alkenyl group, a cycloalkenyl group, an aryl group, an aralkyl group, or a heterocyclic group, with the proviso that each group may have a substituent. Also, in the formula, the two $R^3$s may be united to form an alkylene group, a cycloalkylene group or an arylene group).

Also, the present invention relates to a process for producing the above-mentioned phosphonamide compound, characterized by subjecting an amine compound or an ammonium salt compound and a phosphoryl compound to a reaction for phosphorus—nitrogen bond formation in the presence of a basic compound.

Furthermore, the present invention relates to a process for producing the above-mentioned phosphonamide compound, characterized by subjecting a phosphoric amide compound and an organometallic compound to a reaction for phosphorus—carbon bond formation.

Still furthermore, the present invention relates to a process for producing the above-mentioned phosphonamide compound, characterized by subjecting a phosphonamide compound and an organic compound having a leaving group to a reaction for nitrogen—carbon bond formation.

Also, the present invention relates to an agent for extracting a rare earth metal ion, comprising the above-mentioned phosphonamide compound.

Furthermore, the present invention relates to a process for extracting a rare earth ion from an aqueous solution containing a rare earth metal ion, characterized by using the above-mentioned phosphonamide compound as an extraction agent.

Still furthermore, the present invention relates to a process for back-extracting a rare earth metal ion, characterized by that an organic solvent layer comprising an extracted rare earth metal ion is mixed and contacted with a water, whereby the metal ion is transferred to an aqueous layer.

BEST MODE FOR CARRYING OUT THE INVENTION

In the above-mentioned general formula [1], as the alkyl group in the case where $R^1$ is an alkyl group which may have a substituent, for example, a linear or branched alkyl group having 1 to 40 carbon atoms, preferably, 1 to 30 carbon atoms, more preferably, 1 to 18 carbon atoms is included, and specifically, for example, a methyl group, an ethyl group, an n-propyl group, an isopropyl group, an n-, iso-, sec-, or tert-butyl group, an n-, iso-, sec-, tert-, or neo-pentyl group, an n-hexyl group, an n-octyl group, a 2-octyl group, a 2-ethyl hexyl group, an n-nonyl group, an n-decyl group, an n-dodecyl group, a cetyl group and the like are included.

Also, as the cycloalkyl group in the case where $R^1$ is a cycloalkyl group which may have a substituent, for example, a monocyclic or multicyclic cycloalkyl group having 5 to 30 carbon atoms, preferably, 5 to 20 carbon atoms, more preferably, 5 to 10 carbon atoms is included, and specifically, a cyclopentyl group, a cyclohexyl group, a cyclooctyl group and the like are included.

As the alkenyl group in the case where $R^1$ is an alkenyl group which may have a substituent, for example, the one in which the above-mentioned alkyl group having 2 or more carbon atoms has at least one double bond is included, and specifically, for example, a vinyl group, an allyl group, a 1-propenyl group, an isopropenyl group, a 2-butenyl group, a 1,3-butadienyl group, a 2-pentenyl group, a 2-hexenyl group and the like are included.

As the cycloalkenyl group in the case where $R^1$ is a cycloalkenyl group which may have a substituent, for example, the one in which the above-mentioned cycloalkyl group has at least one unsaturated bond such as double bond, and specifically, for example, a cyclopentenyl group, a cyclohexenyl group and the like are included.

As the alkynyl group in the case where $R^1$ is an alkynyl group which may have a substituent, for example, the one in which the above-mentioned alkyl group having 2 or more carbon atoms has at least one unsaturated bond such as triple bond is included, and specifically, for example, an ethynyl group, a 1-propynyl group, a 2-propynyl group and the like are included.

As the aryl group in the case where $R^1$ is an aryl group which may have a substituent, for example, a monocyclic, polycyclic or condensed cyclic aryl group having 6 to 42 carbon atoms, preferably, 6 to 26 carbon atoms, more preferably, 6 to 22 carbon atoms is included, and specifically, a phenyl group, a naphthyl group, a biphenyl group and the like are exemplified.

As the aralkyl group in the case where $R^1$ is an aralkyl group which may have a substituent, for example, a monocyclic, polycyclic or condensed cyclic aralkyl group having 7 to 30 carbon atoms, preferably, 7 to 20 carbon atoms, more preferably, 7 to 15 carbon atoms is included, and specifically, a benzyl group, a phenethyl group, a naphthylmethyl group, a naphthylethyl group and the like are exemplified.

As the heterocyclic group in the case where $R^1$ is a heterocyclic group which may have a substituent, for example, a saturated or unsaturated monocyclic, polycyclic or condensed cyclic heterocyclic group having at least one nitrogen atom, oxygen atom or sulfur atom in the ring in which one ring is a 5 to 20-membered ring, preferably, 5 to 10-membered ring, more preferably, 5 to 7-membered ring, and the above-mentioned cycloalkyl group, cycloalkenyl group or aryl group may be condensed is included, and specifically, a pyridyl group, a thienyl group, a phenylthienyl group, a thiazolyl group, a furyl group, a piperidyl group, a piperazyl group, a pyrrolyl group, a morpholino group, a imidazolyl group, a indolyl group, a quinolyl group, a pyrimidinyl group and the like are exemplified.

As the substituent of an alkyl group, a cycloalkyl group, an alkenyl group, a cycloalkenyl group, an alkynyl group, an aryl group, an aralkyl group and a heterocyclic group, any substituent may be used as long as it does not interfere with a process for producing the compound of the present invention and does not have an adverse effect when the phosphonamide compound represented by the general formula [1] is used as an agent for extracting a rare earth metal ion. For example, an alkoxy group composed of the above-mentioned alkyl group (such as a methoxy group, an ethoxy group, an isopropoxy group, a tert-butoxy group, a 2-ethylhexyloxy group or an octyloxy group), an alkylthio group (such as a methylthio group or an ethylthio group), a dialkylamino group (such as a dimethylamino group or a diethylamino group), a trisubstituted silyl group (such as a trimethylsilyl group, a triethylsilyl group, a tert-butyldimethylsilyl group or a triphenylsilyl group), a trisubstituted siloxy group (such as a trimethylsiloxy group, a triethylsiloxy group, a tert-butyldimethylsiloxy group or a triphenylsiloxy group), a halogen atom such as chlorine, bromine, fluorine or iodine, an alkylenedioxy group such as a methylenedioxy group or a dimethylmethylenedioxy group, a cyano group and the like are included.

Also, in the case where, in $R^1$ in the general formula [1], the above-mentioned alkyl group, cycloalkyl group, alkenyl group, cycloalkenyl group, alkynyl group, aryl group, aralkyl group, and heterocyclic group can be substituted one another, these groups may be substituted one another. As such, for example, an alkyl-substituted cycloalkyl group, an alkyl-substituted aryl group, an alkyl-substituted cycloalkenyl group, an alkyl-substituted aralkyl group, a cycloalkyl-substituted alkyl group, a cycloalkyl-substituted alkenyl group, a cycloalkyl-substituted alkynyl group, an alkenyl-substituted aryl group, an aryl-substituted alkenyl group, an aryl-substituted alkynyl group and the like are included.

In the general formula [1], definitions and specific examples of the alkyl group in the case where $R^2$ is an alkyl group which may have a substituent, the cycloalkyl group in the case of a cycloalkyl group which may have a substituent, the alkenyl group in the case of an alkenyl group which may have a substituent, the cycloalkenyl group in the case of a cycloalkenyl group which may have a substituent, the aryl group in the case of an aryl group which may have a substituent, the aralkyl group in the case of an aralkyl group which may have a substituent and the heterocyclic group in the case of a heterocyclic group which may have a substituent, and definitions and specific examples of the substituents for these are exactly the same as those described above for $R^1$, respectively.

Also, in the general formula [1], definitions and specific examples of the alkyl group in the case where $R^3$ is an alkyl group which may have a substituent, the cycloalkyl group in the case of a cycloalkyl group which may have a substituent, the alkenyl group in the case of an alkenyl group which may have a substituent, the cycloalkenyl group in the case of a cycloalkenyl group which may have a substituent, the aryl group in the case of an aryl group which may have a substituent, the aralkyl group in the case of an aralkyl group which may have a substituent and the heterocyclic group in the case of a heterocyclic group which may have a substituent, and definitions and specific examples of the substituents for these are exactly the same as those described above for $R^1$, respectively.

Also, as the alkylene group, the cycloalkylene group or the arylene group in the case where two $R^3$s, in the formula, are united to form an alkylene group, a cycloalkylene group or an arylene group, a divalent group which is formed by removal of one hydrogen atom from the above-mentioned alkyl group, cycloalkyl group and aryl group, respectively, is included. As the alkylene group, for example, a linear or branched alkylene group having 1 to 20 carbon atoms, preferably, 1 to 10 carbon atoms, more preferably, 1 to 6 carbon atoms is included, and more specifically, for example, a methylene group, an ethylene group, a trimethylene group, a methylethylene group, a tetramethylene group, a 1,2-dimethylethylene group, a pentamethylene group, a hexamethylene group and the like are included.

As the cycloalkylene group, for example, a monocyclic, polycyclic or condensed cyclic cycloalkylene group having 3 to 30 carbon atoms, preferably, 3 to 20 carbon atoms, more preferably, 3 to 10 carbon atoms is included, and more specifically, a cyclopropylene group, a cyclopentylene group, a cyclohexylene group, a cyclooctylene group and the like are included.

As the arylene group, a monocyclic, polycyclic or condensed cyclic divalent aromatic hydrocarbon group having 6 to 30 carbon atoms, preferably, 6 to 20 carbon atoms, more preferably, 6 to 14 carbon atoms is included, and more specifically, for example, a phenylene group, a tolylene group, a xylylene group, a naphthylene group, a methylnaphthylene group, a biphenylene group and the like are included.

The phosphonamide compound of the present invention represented by the general formula [1] can be produced by subjecting an amine compound or an ammonium salt compound and a phosphoryl compound to a reaction for phosphorus-nitrogen bond formation in the presence of a basic compound.

As the phosphoryl compound used in the above-mentioned production process, for example, a compound represented by the following general formula [2]

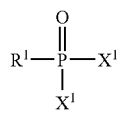

[2]

(wherein $R^1$ is the same as above; $X^1$ represents a leaving group) is included.

Also, as the amine compound used in the above-mentioned production process, for example, a compound represented by the following general formula [3]

$R^2R^4NH$ [3]

(wherein $R^2$ is the same as above; $R^4$ represents a hydrogen atom, an alkyl group, a cycloalkyl group, an alkenyl group, a cycloalkenyl group, an aryl group, an aralkyl group, or a heterocyclic group, with the proviso that each group may have a substituent), a compound represented by the following general formula [4]

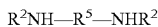

$R^2NH-R^5-NHR^2$ [4]

(wherein $R^2$ is the same as above; $R^5$ represents an alkylene group, a cycloalkylene group or an arylene group), and the like are included.

Further, as the ammonium salt compound used in the above-mentioned production process, for example, a compound represented by the following general formula [5]

$R^2R^4NH_2X^2$ [5]

(wherein $R^2$ and $R^4$ are the same as above; $X^2$ represents an anion group), a compound represented by the following general formula [6]

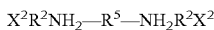

$X^2R^2NH_2-R^5-NH_2R^2X^2$ [6]

(wherein $R^2$, $R^5$ and $X^2$ are the same as above), and the like are included.

In the above-mentioned general formula [2], the leaving group represented by $X^1$ is not specifically limited as long as it can easily be replaced to form a new phosphorus-nitrogen bond by the production process of the present invention, and, for example, a halogen atom such as chlorine, bromine, or iodine, an alkoxy group such as a methoxy group, an ethoxy group, an isopropoxy group or a tert-butoxy group, an aryloxy group such as a phenoxy group or a naphthoxy group, an alkylthio group such as a methylthio group or an ethylthio group, an arylthio group such as a phenylthio group, a tolylthio group or a naphtylthio group and the like are included.

The alkyl group represented by $R^4$ which may have a substituent and other monovalent groups in the above-mentioned general formulae [3] and [5], and the alkylene group represented by $R^5$ and other divalent groups in the general formulae [4] and [6], correspond to a monovalent group and a divalent group represented by $R^3$ in the above-mentioned general formula [1], respectively.

In the above-mentioned general formulae [5] and [6], as the anion group represented by $X^2$, for example, besides a halide ion such as a chloride ion, a bromide ion or an iodide ion, various anion groups such as a hypochlorite ion, a perchlorate ion, a trifluoromethanesulfonate ion, a pentafluorobenzenesulfonate ion, a tetrafluoroborate ion, a hexafluorophosphate ion, a p-toluenesulfonate ion, a benzenesulfonate ion, a methanesulfonate ion, a hydroxide ion, a trifluoroacetate ion, a pentafluorobenzoate ion, an acetate ion, a benzoate ion and a tartrate ion are included.

In the reaction of the compound represented by the general formula [2] with the compound represented by the general formula [3] or the compound represented by the general formula [2] with the compound represented by the general formula [5], the equivalent weight of the used compound represented by the general formula [3] or the general formula [5] is not limited, however, it is generally 1.5 to 20 equivalent, preferably, 2 to 10 equivalent relative to the compound represented by the general formula [2].

In the reaction of the compound represented by the general formula [2] with the compound represented by the general formula [4] or the compound represented by the general formula [2] with the compound represented by the general formula [6], the equivalent weight of the used compound represented by the general formula [4] or the general formula [6] is not limited, however, it is generally 0.5 to 10 equivalent, preferably, 1 to 5 equivalent relative to the compound represented by the general formula [2].

The reaction of the compound represented by the general formula [2] with the compound represented by any of the general formulae [3] to [6] can be performed at various temperatures in any cases, however, it is generally performed at −100 to 180° C., preferably at −70 to 150° C.

In the reaction of the compound represented by the general formula [2] with the compound represented by any of the general formulae [3] to [6], it is preferable to use a solvent in any cases.

As the solvent, various hydrocarbon solvents, ether solvents, aprotic high-polar solvents can be used. As the specific examples, for example, hexane, decane, benzene, toluene, xylene, diethyl ether, tetrahydrofuran, dioxane, N,N-dimethylformamide, acetonitrile, benzonitrile, hexamethylphosphoric triamide, dimethylsulfoxide and the like are included. The amount of the solvent to be used is not limited, however, it is generally 0.1 to 100 mL, preferably, 1 to 20 mL relative to 1 mmol of the compound represented by the general formula [2]. Also, in the case where the base to be used is in the form of a liquid at the above-mentioned reaction temperature, this can be used as the solvent.

In the reaction of the compound represented by the general formula [2] with the compound represented by any of the general formulae [3] to [6], a favorable reaction rate is achieved by using a base in any cases.

As the base, various inorganic or organic bases can be used. As the specific examples, for example, lithium carbonate, sodium carbonate, potassium carbonate, lithium hydroxide, sodium hydroxide, potassium hydroxide, lithium acetate, sodium acetate, potassium acetate, magnesium oxide, calcium oxide, barium hydroxide, trilithium phosphate, trisodium phosphate, tripotassium phosphate, cesium fluoride, cecium carbonate, aluminum oxide, trimethylamine, triethylamine, tributylamine, N,N,N',N'-tetramethylethylenediamine, diisopropylethylamine, N-methylpiperidine, 2,2,6,6-tetramethyl-N-methylpiperidine, pyridine, 4-dimethylaminopyridine, N-methylmorpholine, sodium ethoxide, potassium tert-butoxide and the like are included.

With respect to the amount of the base to be used, it is used at a ratio of 0.01 to 100 equivalent, preferably, 0.1 to 20 equivalent relative to the compound represented by the general formula [2]. Also, each of these bases may be used solely, or plural bases may be used in combination as needed. Furthermore, the compound represented by the above-mentioned general formula [3] or [4] can be favorably used as the base.

The phosphonamide compound of the present invention represented by the general formula [1] can be also produced by the reaction for carbon-phosphorus bond formation between a phosphoric amide compound and an organometallic compound.

As the phosphoric amide compound used in the above-mentioned production process, for example, a compound represented by the following general formula [7]

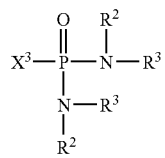

[7]

(wherein $R^2$ and $R^3$ are the same as above; $X^3$ represents a leaving group) is included.

Also, as the organometallic compound used in the above-mentioned production process, for example, a compound represented by the following general formula [8]

R$^1$-M [8]

(wherein $R^1$ is the same as above; M represents a metallo group) is included.

In the above-mentioned general formula [7], the leaving group represented by $X^3$ is not specifically limited as long as it can easily be replaced to form a new carbon-phosphorus bond by the production process of the present invention, and, for example, a halogen atom such as chlorine, bromine, or iodine, an alkoxy group such as a methoxy group, an ethoxy group, an isopropoxy group or a tert-butoxy group, an aryloxy group such as a phenoxy group or a naphthoxy group, an alkylthio group such as a methylthio group or an ethylthio group, an arylthio group such as a phenylthio group, a tolylthio group or a naphtylthio group and the like are included.

In the above-mentioned general formula [8], as the metallo group represented by M, a metal in Group 1 or 2 of the periodic table or a derivative thereof is included, and as the specific examples, for example, a lithio group, a chloromagnesio group, a bromomagnesio group, an iodomagnesio group and the like are included.

In the reaction of the compound represented by the general formula [7] with the compound represented by the general formula [8], the equivalent weight of the used compound represented by the general formula [8] is not limited, however, it is generally 0.5 to 10 equivalent, preferably, 1 to 5 equivalent relative to the compound represented by the general formula [7].

The reaction of the compound represented by the general formula [7] with the compound represented by the general formula [8] can be performed at various temperatures, however, it is generally performed at −100 to 180° C., preferably at −70 to 150° C.

In the reaction of the compound represented by the general formula [7] with the compound represented by the general formula [8], it is preferable to use a solvent.

As the solvent, various hydrocarbon solvents, ether solvents, aprotic high-polar solvents can be used. As the specific examples, for example, hexane, decane, benzene, toluene, xylene, diethyl ether, tetrahydrofuran, dioxane, hexamethylphosphoric triamide and the like are included. The amount of the solvent to be used is not limited, however, it is generally 0.1 to 100 mL, preferably, 1 to 20 mL relative to 1 mmol of the compound represented by the general formula [5].

The phosphonamide compound of the present invention represented by the general formula [1] can be also produced by subjecting an acidic phosphonamide compound and an organic compound having a leaving group to a reaction for carbon-nitrogen bond formation.

Incidentally, the acidic phosphonamide compound according to the present invention is a phosphonamide compound having one or more hydrogen atoms attached to the nitrogen atom.

As the acidic phosphonamide compound used in the above-mentioned production process, for example, a compound represented by the following general formula [9]

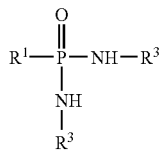

[9]

(wherein $R^1$ and $R^3$ are the same as above) is included.

As the organic compound having a leaving group used in the above-mentioned production process, a compound represented by the following general formula [10]

R$^2$—X$^4$ [10]

(wherein $X^4$ represents a leaving group; $R^2$ is the same as above) is exemplified.

In the above-mentioned general formula [10], the leaving group represented by $X^4$ is not specifically limited as long as it can easily be replaced to form a new carbon-nitrogen bond by the production process of the present invention, and, besides a halogen atom such as a chlorine atom, a bromine atom or an iodine atom, various leaving groups including an iodonio group such as an acetoxyphenyliodonio group or a phenyl(trifluoromethanesulfoxy)iodonio group, a sulfonyl group such as a methanesulfonyl group or a trifluoromethanesulfonyl group and the like are exemplified.

In the reaction of the compound represented by the general formula [9] with the compound represented by the general formula [10], a favorable reaction rate is achieved by using a base.

As the base, besides the above-mentioned bases in the reaction of the compound represented by the above-mentioned general formula [2] with the compound represented by any of the above-mentioned general formulae [3] to [6], a metal hydride compound such as sodium hydride or lithium aluminum hydride, a metal amide compound such as lithium diisopropylamide, lithium amide or sodium amide, an organometallic compound represented by the above-mentioned general formula [8] (wherein $R^1$ and M are the same as above) and the like are included. With respect to the amount of the base to be used, it is used at a ratio of 0.01 to 100 equivalent, preferably, 0.1 to 20 equivalent relative to the compound represented by the general formula [9]. Also, each of these bases may be used solely, or plural bases may be used in combination as needed.

The equivalent weight of the used compound represented by the general formula [10] in the reaction of the compound represented by the general formula [9] with the compound represented by the general formula [10] is not limited, and, it is generally 1.5 to 10 equivalent, preferably, 2 to 5 equivalent relative to the compound represented by the general formula [9].

The reaction of the compound represented by the general formula [9] with the compound represented by the general formula [10] can be performed at various temperatures, however, it is generally performed at −100 to 180° C., preferably at −70 to 150° C.

In the reaction of the compound represented by the general formula [9] with the compound represented by the general formula [10], it is preferable to use a solvent.

As the solvent, various hydrocarbon solvents, ether solvents, aprotic high-polar solvents can be used. As the specific examples, for example, hexane, decane, benzene, toluene, xylene, diethyl ether, tetrahydrofuran, dioxane, hexamethylphosphoric triamide, acetonitrile and the like are included. The amount of the solvent to be used is not limited, however, it is generally 0.1 to 100 mL, preferably, 1 to 20 mL relative to 1 mmol of the compound represented by the general formula [9].

A produced phosphonamide compound can be purified by a common process such as distillation, column chromatography, and recrystallization in any cases.

The phosphonamide compound of the present invention can be used as an agent for extracting a rare earth metal.

A process for extracting a rare earth metal by using the phosphonamide compound of the present invention as an extraction agent is performed by mixing and contacting an aqueous solution containing a rare earth metal ion, a phosphonamide compound represented by the above-mentioned general formula [1] and an organic solvent at a suitable temperature with the use of means such as stirring or shaking, and conducting layer separation into an organic layer (an extraction agent layer) and an aqueous layer.

As the organic solvent to be used for extraction, the one which can dissolve the phosphonamide compound of the present invention and is not completely miscible with water is preferable, and, halogenated hydrocarbons, hydrocarbons, ethers, alcohols, nitro compounds, phosphate esters and the like are exemplified. Specific examples include chloroform, carbon tetrachloride, methyl isobutyl ketone, nitrobenzene, octanol, hexane, octane, decane, dodecane, benzene, toluene, xylene, ethylbenzene, tributyl phosphate and the like.

Each of these organic solvents may be used solely, or plural organic solvents may be used in combination as needed. In the case where a phosphonamide compound represented by the general formula [1] is liquid and is not completely miscible with water, the phosphonamide compound can serve as an organic solvent (extraction solvent).

It is desirable to keep the pH value of the aqueous solution containing a rare earth metal ion, which is used for extraction, at pH 7 or lower by using an appropriate acid. As the acid, various inorganic acids and organic acids are used suitably, and the specific examples include hydrochloric acid, sulfuric acid, nitric acid, acetic acid, oxalic acid, carbonic acid, phosphoric acid, citric acid, tartaric acid, ethylenediaminetetraacetic acid and the like.

Each of these acids may be used solely or plural acids may be used in combination as needed.

The concentration of the rare earth metal ions contained in the aqueous solution, when conducting extraction, is not specifically limited, however, it is generally $1.0 \times 10^{-9}$ to 10 mol/L, preferably, $5.0 \times 10^{-7}$ to 5.0 mol/L.

The number of moles of the phosphonamide compound represented by the general formula [1], which is used for extraction, is not specifically limited, however, it is preferable to be 0.01-fold or more relative to the total amount of the rare earth metal ions.

The volume ratio of the aqueous solution containing a rare earth metal ion to the organic solvent containing a phosphonamide compound, which are used for extraction, is not specifically limited, however, it is generally 0.001:1 to 100:1, preferably, 0.02:1 to 50:1.

The extraction temperature when performing extraction is not specifically limited, however, it is generally 0 to 100° C., preferably 10 to 70° C.

The rare earth metal ion extracted and transferred from an aqueous layer to an organic solvent layer under the extraction conditions can be back-extracted from the organic solvent layer to an aqueous layer by contacting the organic solvent layer with water other than the aqueous layer.

Namely, by mixing and contacting the organic solvent layer comprising the rare earth metal ion extracted by the above-mentioned extraction operation with water, the metal ion can be transferred to an aqueous layer, thereby the rare earth metal ion can be back-extracted into the aqueous layer.

In the back-extraction process of the present invention, as the water to be used for back-extracting a rare earth metal ion from an organic solvent layer comprising an extracted rare earth metal ion, a weakly acidic or acidic water is preferable. Namely, it is preferable that the pH value of the water to be used for the back-extraction be kept at lower than pH 7 by using an appropriate acid. As the acid to be used for the pH adjustment, various inorganic acids and organic acids are included, and the specific examples include hydrochloric acid, sulfuric acid, nitric acid, acetic acid, oxalic acid, carbonic acid, phosphoric acid, citric acid, tartaric acid, ethylenediaminetetraacetic acid and the like. Each of these acids may be used solely or plural acids may be used in combination as needed. The pH adjustment may be performed by using acidic salts, various buffer agents (buffer solutions) or the like, instead of an acid.

The volume ratio of the organic layer to the aqueous layer, which are used for back-extraction is not specifically limited, however, it is generally 0.001:1 to 1000:1, preferably 0.02:1 to 50:1.

The temperature for the back-extraction is not specifically limited, however, it is generally 0 to 100° C., preferably 10 to 70° C.

Incidentally, all the content described in the specification, JP-A-2002-057419, is incorporated in this description.

EXAMPLES

Hereunder, the present invention will be explained in more detail with reference to Examples, however, the present invention is not limited to these Examples.

Example 1

In a glass container, 1.44 g (10 mmol) of N,N'-diisopropylethylenediamine (in the general formula [4], $R^2$=a isopropyl group, $R^5$=an ethylene group), 0.24 g (2 mmol) of 4-dimethylaminopyridine and 3 mL of triethylamine were dissolved in 50 mL of tetrahydrofuran and the container was soaked in a water bath. Thereto was added 1.95 g (10 mmol) of dichlorophenylphosphonic acid (in the general formula [2], $R^1$=a phenyl group and $X^1$=a chlorine atom) little by little and stirred for 5 hours. The obtained reaction mixture was filtrated, and 1.94 g (7.3 mmol) of 2,5-diaza-2,5-diisopropyl-1-oxo-1-phenylphosphorane (in the general formula [1], $R^1$=a phenyl group, $R^2$=an isopropyl group and two $R^3$s are united to form an ethylene group) was obtained by distillation under a reduced pressure (180° C./2 mmHg) of the residue, which was obtained by concentrating the filtrate under a reduced pressure. This compound is a novel compound which has not been described in a published article.

The spectral data and the results of the elementary analysis of the compound obtained in Example 1 are as follows.

$^1$H-NMR(CDCl$_3$):δ0.85-0.90(6H,m), 1.07-1.22(6H,m), 3.12-3.19(2H,m), 3.26-3.35(4H, m), 7.32-7.38(3H,m), 7.71-7.79(2H,m)ppm.

$^{13}$C-NMR(CDCl$_3$):δ20.5(d,J=4.3 Hz) 21.5(d,J=2.3 Hz), 39.9(d,J=9.8 Hz), 44.6(d,J=6.2 Hz), 128.0(d,J=30.5 Hz), 128.7(d,J=156.7 Hz), 131.0(d,J=2.9 Hz), 132.8(d,J=13.3 Hz)ppm.

$^{31}$P-NMR(CDCl$_3$):δ24.3 ppm.

MS(EI):m/z 266.77.

Elementary analysis, calculated as $C_{14}H_{23}ON_2P$: C, 63.14; H, 8.70; N, 10.52%. Found: C, 63.02; H, 8.81; N, 10.45%.

Example 2

In a glass container, 1.44 g (10 mmol) of N,N'-dipropylethylenediamine (in the general formula [4], $R^2$=a propyl group and $R^3$=an ethylene group), 0.24 g (2 mmol) of 4-dimethylaminopyridine and 3 mL of triethylamine were dissolved in 50 mL of tetrahydrofuran and the container was soaked in a water bath. Thereto was added 1.95 g (10 mmol) of dichlorophenylphosphonic acid (in the general formula [2], $R^1$=a phenyl group and $X^1$=a chlorine atom) little by little and stirred for 5 hours. The obtained reaction mixture was filtrated, and 1.51 g (5.7 mmol) of 2,5-diaza-2,5-dipropyl-1-oxo-1-phenylphosphorane (in the general formula [1], $R^1$=a phenyl group, $R^2$=a propyl group and two $R^3$s are united to form an ethylene group) was obtained by distillation under a reduced pressure (180° C./2 mmHg) of the residue, which was obtained by concentrating the filtrate under a reduced pressure. This compound is a novel compound which has not been described in a published article.

The spectral data and the results of the elementary analysis of the compound obtained in Example 2 are as follows.

$^1$H-NMR(CDCl$_3$):δ0.76(6H,t,J=7.3 Hz), 1.37-1.49(4H, m), 2.67-2.75(4H,m), 3.20-3.31(2H, m), 3.37-3.40(2H,m), 7.38-7.43(3H,m), 7.68-7.72(2H,m)ppm.

$^{13}$C-NMR(CDCl$_3$):δ11.7, 21.7(d,J=4.1 Hz), 45.7(d,J=9.3 Hz), 46.9(d,J=5.2 Hz), 128.1(d,J=13.4 Hz), 131.2(d,J=3.1 Hz), 132.4(d,J=156.3 Hz), 132.5(d,J=9.3 Hz)ppm.

$^{31}$P-NMR(CDCl$_3$):δ28.3 ppm.

MS(EI):m/z 266.77.

Elementary analysis, calculated as $C_{14}H_{23}ON_2P$: C, 63.14; H, 8.70; N, 10.52%. Found: C, 63.08; H, 8.76; N, 10.47%.

Example 3

In a glass container, 2.12 g (10 mmol) of N,N'-diphenylethylenediamine (in the general formula [4], $R^2$=a phenyl group and $R^5$=an ethylene group), 0.24 g (2 mmol) of 4-dimethylaminopyridine and 3 mL of triethylamine were dissolved in 50 mL of tetrahydrofuran and the container was soaked in a water bath. Thereto was added 1.95 g (10 mmol) of dichlorophenylphosphonic acid (in the general formula [2], $R^1$=a phenyl group and $X^1$=a chlorine atom) little by little and stirred for 5 hours. The obtained reaction mixture was filtrated, and 2.56 g (7.70 mmol) of 2,5-diaza-1-oxo-1,2,5-triphenylphosphorane (in the general formula [1], $R^1$=$R^2$=a phenyl group and two $R^3$s are united to form an ethylene group) was obtained by distillation under a reduced pressure (180° C./2 mmHg) of the residue, which was obtained by concentrating the filtrate under a reduced pressure. This compound is a novel compound which has not been described in a published article.

The spectral data and the results of the elementary analysis of the compound obtained in Example 3 are as follows.

$^1$H-NMR(CDCl$_3$):δ3.93-4.03(4H,m), 6.92(2H,t,J=7.2 Hz), 7.15-7.24(8H,m), 7.37-7.40(3H, m), 7.81-7.85(2H,m) ppm.

$^{13}$C-NMR(CDCl$_3$):δ43.8(d,J=8.6 Hz), 116.5(d,J=4.8 Hz), 121.8, 128.7(d,J=14.5 Hz), 129.2, 132.1, 132.2(d,J=3.1 Hz), 132.5(d,J=10.7 Hz), 141.3(d,J=7.6 Hz)ppm.

$^{31}$P-NMR(CDCl$_3$):δ18.8 ppm.

MS(EI):m/z 334.77.

Elementary analysis, calculated as $C_{20}H_{19}ON_2P$: C, 71.85; H, 5.73; N, 8.38%. Found: C, 71.83; H, 5.64; N, 8.30%.

Example 4

In a glass container, 4.11 g (20 mmol) of p-octylaniline (in the general formula [3], $R^2$=a p-octylphenyl group and $R^4$=a hydrogen atom) and 3 mL of triethylamine were dissolved in 50 mL of acetonitrile and the container was soaked in a water bath. Thereto was added 1.95 g (10 mmol) of dichlorophenylphosphonic acid (in the general formula [2], $R^1$=a phenyl group and $X^1$=a chlorine atom) little by little, stirred for 1 hour, and then further stirred for 1 hour under heated reflux. The obtained reaction mixture was filtrated, and 3.19 g (5.98 mmol) of N,N'-bis(p-octylphenyl)phenylphosphonamide (in the general formula [1], $R^1$=a phenyl group, $R^2$=a p-octylphenyl group and $R^3$=a hydrogen atom) was obtained by recrystallization of the obtained solid substance from ethyl acetate. This compound is a novel compound which has not been described in a published article.

The spectral data and the results of the elementary analysis of the compound obtained in Example 4 are as follows.

$^1$H-NMR(CDCl$_3$):δ0.87(6H,t,J=7.0 Hz), 1.25(20H,brs), 1.50-1.54(4H,m), 2.48(4H,t,J=7.5 Hz), 5.38(2H,d,J=9.6 Hz), 6.94(8H,s), 7.39-7.48(2H,m), 7.49-7.55(1H,m), 7.90(2H,dd, J=6.9, 13.4 Hz)ppm.

$^{13}$C-NMR(CDCl$_3$): δ 14.1, 22.6, 29.2, 29.4, 30.9, 31.5, 31.9, 35.1, 118.5(d,J=6.2 Hz), 128.7(d, J=13.5 Hz), 129.1, 130.4(d,J=173.7 Hz), 131.7(d,J=10.3 Hz), 132.3, 136.6, 137.5 ppm.

$^{31}$P-NMR(CDCl$_3$):δ10.0 ppm.

Elementary analysis, calculated as C$_{34}$H$_{49}$ON$_2$P: C, 76.65; H, 9.27; N, 5.26%. Found: C, 76.86; H, 9.27; N, 5.15%.

Example 5

In a glass container, 6.63 g (30 mmol) of p-octyloxyaniline (in the general formula [3], R$^2$=a p-octyloxyphenyl group and R$^4$=a hydrogen atom) and 9 mL of triethylamine were dissolved in 60 mL of acetonitrile and the container was soaked in a water bath. Thereto was added 2.93 g (15 mmol) of dichlorophenylphosphonic acid (in the general formula [2], R$^1$=a phenyl group and X$^1$=a chlorine atom) little by little, stirred for 1 hour, and then further stirred for 1 hour under heated reflux. The obtained reaction mixture was filtrated, and 4.88 g (7.60 mmol) of N,N'-bis(p-octyloxyphenyl)phenylphosphonamide (in the general formula [1], R$^1$=a phenyl group, R=a p-octyloxyphenyl group and R$^3$=a hydrogen atom) was obtained by recrystallization of the obtained solid substance from ethyl acetate. This compound is a novel compound which has not been described in a published article.

The spectral data and the results of the elementary analysis of the compound obtained in Example 5 are as follows.

$^1$H-NMR(CDCl$_3$):δ0.88(6H,t,J=6.9 Hz), 1.28(16H,brs), 1.36-1.41(4H,m), 1.70-1.77(4H,quin, J=7.5 Hz), 5.11(2H,d, J=9.1 Hz), 6.71(4H,d,J=8.4 Hz), 6.98(4H,d,J=8.4 Hz), 7.41-7.43(2H, m), 7.44-7.46(1H,m), 7.83-7.90(2H,m)ppm.

$^{13}$C-NMR(CDCl$_3$):δ14.1, 22.6, 26.0, 29.2, 29.3, 29.7, 31.8, 68.3, 115.2, 120.8(d,J=6.2 Hz), 128.6(d,J=13.5 Hz), 131.6(d,J=157.2 Hz), 131.6(d,J=10.4 Hz), 132.2, 132.7, 154.7 ppm.

$^{31}$P-NMR(CDCl$_3$):δ10.9 ppm.

Elementary analysis, calculated as C$_{34}$H$_{49}$O$_3$N$_2$P: C, 72.31; H, 8.75; N, 4.96%. Found: C, 72.64; H, 8.92; N, 4.97%.

Example 6

In a glass container, 6.69 g (10 mmol) of N,N'-dicetylethylenediamine dihydrobromide (in the general formula [6], R$^2$=a cetyl group, R$^5$=an ethylene group and X$^2$=a bromide ion), 0.24 g (2 mmol) of 4-dimethylaminopyridine and 3 mL of triethylamine were dissolved in 50 mL of tetrahydrofuran and the container was soaked in a water bath. Thereto was added 1.95 g (10 mmol) of dichlorophenylphosphonic acid (in the general formula [2], R$^1$=a phenyl group and X$^1$=a chlorine atom) little by little and stirred for 5 hours. The obtained reaction mixture was filtrated, and 1.58 g (2.5 mmol) of 2,5-diaza-2,5-dicetyl-1-oxo-1-phenylphosphorane (in the general formula [1], R$^1$K=a phenyl group, R$^2$=a cetyl group and two R$^3$s are united to form an ethylene group) was obtained by purifying the residue, which was obtained by concentrating the filtrate under a reduced pressure, by silica gel column chromatography using hexane as an eluent. This compound is a novel compound which has not been described in a published article.

The spectral data and the results of the elementary analysis of the compound obtained in Example 6 are as follows.

$^1$H-NMR(CDCl$_3$): δ 0.84(6H,t,J=6.9 Hz), 1.13(4H,brs), 1.25(48H,brs), 1.41-1.43(4H,m), 2.76(4H,q,J=7.6 Hz), 3.21-3.30(2H,m), 3.36-3.40(2H,m), 7.32-7.41(3H,m), 7.68-7.80(2H,m) ppm.

$^{13}$C-NMR(CDCl$_3$): δ 14.1, 22.7, 26.8, 28.5(d,J=4.5 Hz), 29.2, 29.4, 29.5, 29.55, 29.63, 29.67, 29.70, 31.9, 45.1(d, J=5.2 Hz), 45.8(d,J=9.4 Hz), 128.2(d,J=13.7 Hz), 131.2, 132.5(d,J=157.0H z), 132.6(d,J=9.8 Hz)ppm.

$^{31}$P-NMR(CDCl$_3$):δ28.4 ppm.

Elementary analysis, calculated as C$_{40}$H$_{75}$ON$_2$P: C, 76.14; H, 11.98; N, 4.44%. Found: C, 76.10; H, 12.15; N, 4.31%.

Example 7

In a glass container, 2.12 g (45 mmol) of N,N'-dicetylethylenediamine (in the general formula [4], R$^2$=a cetyl group and R$^5$=an ethylene group), 0.24 g (9 mmol) of 4-dimethylaminopyridine and 15 mL of triethylamine were dissolved in 200 mL of tetrahydrofuran and the container was soaked in a water bath. Thereto was added 8.78 g (45 mmol) of dichlorophenylphosphonic acid (in the general formula [2], R$^1$=a phenyl group and X$^1$=a chlorine atom) little by little and stirred for 2 hours. The obtained reaction mixture was filtrated, and 14.9 g (22.5 mmol) of 2,5-diaza-2,5-dicetyl-1-oxo-1-phenylphosphorane (in the general formula [1], R$^1$=a phenyl group, R$^2$=a cetyl group and two R$^3$s are united to form an ethylene group) was obtained by purifying the residue, which was obtained by concentrating the filtrate under a reduced pressure, by silica gel chromatography using diethyl ether as an eluent.

Example 8

In a glass container, 0.285 g (1.0 mmol) of 1-bromo-4-octyloxybenzene and 0.030 g (1.25 mmol) of metallic magnesium were mixed in tetrahydrofuran (1 mL), heated to 50° C. and stirred for 30 minutes. The obtained solution of 4-octyloxyphenylmagnesium bromide (in the general formula [8], R$^1$=a 4-octyloxyphenyl group and M=a bromomagnesio group) was mixed with 0.210 g (1.0 mmol) of 2,5-diaza-2,5-dimethyl-1-oxo-1-phenoxy-phosphorane (in the general formula [7], R$^2$=a methyl group, X$^3$=a phenoxy group and two R$^3$s are united to form an ethylene group) and stirred for 7 days at 67° C. To the obtained mixture, 0.2 mL of water was added, and after a solid substance was removed by filtration, the filtrate was concentrated under a reduced pressure. The obtained oily substance was purified by silica gel column chromatography using diethyl ether as an eluent to obtain 0.196 g (0.58 mmol) of 2,5-diaza-2,5-dimethyl-1-(4-octyloxyphenyl)-1-oxophosphorane (in the general formula [1], R$^1$=a 4-octyloxyphenyl group, R$^2$=a methyl group and two R$^3$s are united to form an ethylene group). This compound is a novel compound which has not been described in a published article.

The spectral data of the compound obtained in Example 8 are as follows.

$^1$H-NMR(CDCl$_3$):δ0.88(3H,t,J=6.9 Hz), 1.26-1.31(10H, brs), 1.41-1.45(2H,m), 1.78(2H,quin, J=6.7 Hz), 2.50(6H,d, J=10.1 Hz), 3.19-3.24(2H,m), 3.33-3.38(2H,m), 3.98(2H,t, J=6.7H z), 6.92(2H,dd,J=2.6, 8.6 Hz), 7.62(2H,dd,J=8.6, 12.3 Hz)ppm.

$^{13}$C-NMR(CDCl$_3$):δ14.1, 22.7, 26.0, 29.2, 29.3, 31.7(d, J=5.6 Hz), 48.6, 68.1, 114.4(d,J=14.8 Hz), 120.5, 134.5(d, J=11.3 Hz), 162.0 ppm.

$^{31}$P-NMR(CDCl$_3$): δ 30.2 ppm.

MS(EI):m/z 338.

Elementary analysis, calculated as C$_{18}$H$_{31}$O$_2$N$_2$P: C, 63.88; H, 9.23; N, 8.28%. Found: C, 63.57; H, 9.45; N, 8.19%.

Example 9

In a glass container, 1.68 g (5.0 mmol) of N,N'-bis(p-methylphenyl)phenylphosphonamide (in the general formula [9], $R^1$=a phenyl group and $R^3$=a p-methylphenyl group), 3 mL of octyl bromide (in the general formula [10], $R^2$=an octyl group and $X^4$=a bromine atom), 0.9 g of sodium hydride and 30 mL of acetonitrile were mixed and the mixture was stirred for 24 hours at room temperature. After a solid substance was removed by filtrating the reaction mixture, 2.41 g (4.56 mmol) of N,N'-bis(p-methylphenyl)-N,N'-dioctylphenylphosphonamide (in the general formula [1], $R^1$=a phenyl group, $R^2$=an octyl group and $R^3$=a p-methylphenyl group) was obtained by purifying the residue, which was obtained by concentrating the filtrate, by silica gel chromatography using ether as an eluent. This compound is a novel compound which has not been described in a published article.

The spectral data of the compound obtained in Example 9 are as follows.

$^1$H-NMR(CDCl$_3$): δ 0.83(6H,t,J=6.9 Hz), 0.95-1.43(24H, m), 2.29(6H,s), 3.17-3.23(2H,m), 3.29-3.35(2H,m), 6.95 (4H,d,J=8.0 Hz), 7.02(4H,d,J=8.0 Hz), 7.34-7.41(3H,m), 7.71-7.78(2H,m)ppm.

$^{13}$C-NMR(CDCl$_3$):δ14.0, 20.9, 22.6, 26.7, 28.5(d,J=3.1 Hz), 29.1, 29.2, 31.7, 50.5(d,J=4.1 Hz), 127.9(d,J=13.5 Hz), 128.5(d,J=3.1 Hz), 129.2, 131.0, 132.2(d,J=157.3 Hz), 132.6 (d,J=9.3 Hz), 135.0, 140.0(d,J=2.0 Hz)ppm.

$^{31}$P-NMR(CDCl$_3$):δ21.3 ppm.

Elementary analysis, calculated as $C_{36}H_{53}ON_2P$: C, 77.10; H, 9.53; N, 5.00%. Found: C, 77.24; H, 9.56; N, 4.99%.

Example 10

In the same manner as in Example 9 except using 1.84 g (5.0 mmol) of N,N'-bis(p-methoxyphenyl)phenylphosphonamide (in the general formula [9], $R^1$=a phenyl group and $R^3$=a p-methoxyphenyl group) instead of N,N'-bis(p-methylphenyl)phenylphosphonamide in Example 9, 1.34 g (3.40 mmol) of N,N'-bis(p-methoxyphenyl)-N,N'-dioctylphenylphosphonamide (in the general formula [1], $R^1$=a phenyl group, $R^2$=an octyl group and $R^3$=a p-methoxyphenyl group) was obtained. This compound is a novel compound which has not been described in a published article.

The spectral data of the compound obtained in Example 10 are as follows.

$^1$H-NMR(CDCl$_3$): δ 0.83(6H,t,J=7.2 Hz), 0.94-1.23(24H, m), 3.08-3.22(2H,m), 3.23-3.26 (2H,m), 3.76(6H,s), 6.74 (4H,d,J=7.9 Hz), 6.94(4H,d,J=7.9 Hz), 7.31-7.48(3H,m), 7.70-7.76 (2H,m)ppm.

$^{13}$C-NMR(CDCl$_3$): δ 14.0, 22.6, 26.7, 28.5(d,J=3.1 Hz), 29.1, 29.2, 31.7, 50.7(d,J=4.1 Hz), 55.3, 113.8, 127.9(d, J=12.4 Hz), 130.1(d,J=3.1 Hz), 130.9(d,J=3.1 Hz), 132.1(d, J=153.1 Hz), 132.7(d,J=8.3 Hz), 135.3(d,J=3.1 Hz), 157.4 ppm.

$^{31}$P-NMR(CDCl$_3$):δ21.7 ppm.

Elementary analysis, calculated as $C_{36}H_{53}O_3N_2P$: C, 72.94; H, 9.01; N, 4.73%. Found: C, 72.90; H, 9.01; N, 5.01%.

Example 11

In a glass container, 3.72 g (7.0 mmol) of N,N'-bis(p-octylphenyl)phenylphosphonamide (in the general formula [9], $R^1$=a phenyl group and $R^3$=a p-octylphenyl group), 5 mL of methyl iodide (in the general formula [10], $R^2$=a methyl group and $X^4$=an iodine atom), 1.0 g of sodium hydride and 100 mL of acetonitrile were mixed and the mixture was stirred for 24 hours at room temperature. After a solid substance was removed by filtrating the reaction mixture, 2.88 g (5.15 mmol) of N,N'-bis(p-octylphenyl)-N,N'-dimethylphenylphosphonamide (in the general formula [1], $R^1$=a phenyl group, $R^2$=a methyl group and $R^3$=a p-octylphenyl group) was obtained by purifying the residue, which was obtained by concentrating the filtrate, by silica gel chromatography using ether as an eluent. This compound is a novel compound which has not been described in a published article.

The spectral data of the compound obtained in Example 11 are as follows.

$^1$H-NMR(CDCl$_3$):0.87(6H,t,J=6.9 Hz), 1.26(20H,brs), 1.53-1.57(4H,m), 2.52(4H,t,J=7.6Hz), 3.05(6H,d,J=9.3 Hz), 6.99(4H,d,J=8.4 Hz), 7.09(4H,d,J=8.4 Hz), 7.26-7.41(3H, m), 7.70-7.76(2H,m)ppm.

$^{13}$C-NMR(CDCl$_3$):δ14.1, 22.7, 29.3, 29.5, 31.5, 31.6(d, J=3.1 Hz), 31.9, 35.3, 38.2(d,J=5.2 Hz), 125.2(d,J=4.2 Hz), 128.1(d,J=13.5 Hz), 128.7(2C), 131.7(d,J=90.0 Hz), 132.6(d, J=9.3 Hz), 139.2, 142.8(d,J=3.1 Hz)ppm.

$^{31}$P-NMR(CDCl$_3$):δ22.5 ppm.

Elementary analysis, calculated as $C_{36}H_{53}ON_2P$: C, 77.10; H, 9.53; N, 5.00%. Found: C, 77.00; H, 9.68; N, 5.03%.

Example 12

In a glass container, 1.13 g (2.0 mmol) of N,N'-bis(p-octyloxyphenyl)phenylphosphonamide (in the general formula [9], $R^1$=a phenyl group and $R^3$=a p-octyloxyphenyl group), 1 mL of methyl iodide (in the general formula [10], $R^3$=a methyl group and $X^4$=an iodine atom), 0.3 g of sodium hydride and 20 mL of acetonitrile were mixed and the mixture was stirred for 24 hours at room temperature. After a solid substance was removed by filtrating the reaction mixture, 0.834 g (1.41 mmol) of N,N'-bis(p-octyloxyphenyl)-N,N'-dimethylphenylphosphonamide (in the general formula [1], $R^1$=a phenyl group, $R^2$=a methyl group and $R^3$=a p-octyloxyphenyl group) was obtained by purifying the residue, which was obtained by concentrating the filtrate, by silica gel chromatography using ether as an eluent. This compound is a novel compound which has not been described in a published article.

The spectral data of the compound obtained in Example 12 are as follows.

$^1$H-NMR(CDCl$_3$): δ 0.88(6H,t,J=6.9 Hz), 1.29(16H,brs), 1.38-1.43(4H,m), 1.74(4H,quin,J=6.6 Hz), 2.99(6H,d,J=10.2 Hz), 3.88(4H,t,J=6.6 Hz), 6.74(4H,d,J=9.0 Hz), 7.07(4H,d, J=9.0 Hz), 7.34-7.39(3H,m), 7.60-7.75(2H,m)ppm.

$^{13}$C-NMR(CDCl$_3$): δ 14.1, 22.6, 29.19, 29.24, 29.3, 31.8, 38.7(d,J=5.2 Hz), 68.1, 114.6, 127.5 (d,J=4.1 Hz), 128.0(d, J=13.4 Hz), 130.8(d,J=157.4 Hz), 131.1(d,J=2.1 Hz), 132.5 (d,J=8.3 Hz), 137.9(d,J=3. Hz), 156.5 ppm.

$^{31}$P-NMR(CDCl$_3$):δ22.6 ppm.

Elementary analysis, calculated as $C_{36}H_{53}O_3N_2P$: C, 72.94; H, 9.01; N, 4.73%. Found: C, 72.85; H, 9.07; N, 4.99%.

Example 13

In a glass container, 0.88 g (10 mmol) of N,N'-dimethylethylenediamine (in the general formula [4], $R^2$=a methyl group and $R^5$=an ethylene group) and 3 mL of triethylamine were dissolved in 50 mL of tetrahydrofuran and the container was soaked in a water bath. Thereto was added 1.95 g (10 mmol) of dichlorophenylphosphonic acid (in the general formula [2], $R^1$=a phenyl group and $X^1$=a chlorine atom) little by little and stirred for 2 hours. The obtained reaction mixture was filtrated, and 1.79 g (8.5 mmol) of 2,5-diaza-2,5-dimethy-1-oxo-1-phenylphosphorane (in the general formula [1], $R^1$=a phenyl group, $R^2$=a methyl group and two $R^3$s are united to form an ethylene group) was obtained by distillation under a reduced pressure (180° C./2 mmHg) of the residue, which was obtained by concentrating the filtrate under a reduced pressure. This compound is a novel compound which has not been described in a published article.

The spectral data of the compound obtained in Example 13 are as follows.

$^1$H-NMR(CDCl$_3$):δ2.44(6H,d,J=7.6 Hz), 3.15-3.23(2H, m), 3.32-3.37(2H,m), 7.38-7.45(3H, m), 7.64-7.71(2H,m) ppm.

$^{13}$C-NMR(CDCl$_3$): δ 31.6(d,J=6.3 Hz), 48.4(d,J=8.8 Hz), 128.3(d,J=13.7 Hz), 131.0(d,J=156.6 Hz), 131.5(d,J=2.9 Hz), 132.5(d,J=9.8 Hz)ppm.

$^{31}$P-NMR(CDCl$_3$): δ 29.5 ppm.

MS(EI):m/z 210.77.

Comparative Example 1

To 4 mL of 1 mol/L nitric acid aqueous solution containing 1.00×10$^{-4}$ mol/L trivalent lanthanum ions and 1.00×10$^{-4}$ mol/L trivalent europium ions, 4 mL of a dichloromethane solution was added and shaken for 10 minutes at 25° C. After the layer separation by centrifugation, the concentrations of trivalent lanthanum ions and trivalent europium ions remaining in the aqueous solution were measured by ICP emission spectrochemical analysis which revealed that all the trivalent lanthanum ions and the trivalent europium ions remained in the aqueous solution.

Examples 14 to 33

To 4 mL of 1 mol/L nitric acid aqueous solution containing 1.00×10$^{-4}$ mol/L trivalent lanthanum ions and 1.00×10$^{-4}$ mol/L trivalent europium ions, 4 mL of a dichloromethane solution containing 1 mmol of various phosphonamide compounds was added and shaken for 10 minutes at 25° C. After the layer separation, the concentrations of trivalent lanthanum ions and trivalent europium ions remaining in the aqueous solution were measured by ICP emission spectrochemical analysis and the extraction ratios of trivalent lanthanum and trivalent europium ions were calculated. The results are shown in Table 1.

Incidentally, in all cases, the extraction ratio described below indicates the ratio of the number of moles of ions transferred from the aqueous layer to the organic layer relative to the number of moles of ions contained in the initial aqueous layer for each ion.

TABLE 1

| | Phosphonamide | Extraction Ratio / % | |
|---|---|---|---|
| | | Lanthanum | Europium |
| Comparative Example 1 | None | 0 | 0 |
| Example 14 | Ph—P(=O)(—N(Me)—(CH$_2$)$_2$—N—Me) | 91.6 | 92.9 |
| Example 15 | Ph—P(=O)(—N(C$_{16}$H$_{33}$)—(CH$_2$)$_2$—N—C$_{16}$H$_{33}$) | 98.6 | 99.5 |
| Example 16 | Ph—P(=O)(—N(C$_3$H$_7$)—(CH$_2$)$_2$—N—C$_3$H$_7$) | 95.1 | 96.7 |
| Example 17 | Ph—P(=O)(—N($^i$C$_3$H$_7$)—(CH$_2$)$_2$—N—$^i$C$_3$H$_7$) | 23.5 | 35.2 |
| Example 18 | Ph—P(=O)(—N(Ph)—(CH$_2$)$_2$—N—Ph) | 2.8 | 7.2 |
| Example 19 | Ph—P(=O)(—N(Me)—(CH$_2$)$_3$—N—Me) | 85.3 | 90.7 |
| Example 20 | Ph—P(=O)(—N(Me)—Me)(—N(Me)) | 75.1 | 84.4 |
| Example 21 | Ph—P(=O)(—N(Ph)—Me)(—N(Ph)—Me) | 16.3 | 36.0 |
| Example 22 | Ph—P(=O)(—N(Ph)—H)(—N(Ph)—H) | 5.8 | 6.0 |
| Example 23 | Ph—P(=O)(—N(C$_6$H$_4$NMe$_2$-p)—H)(—N(C$_6$H$_4$NMe$_2$-p)—H) | 9.9 | 10.1 |

TABLE 1-continued

| | Phosphonamide | Extraction Ratio / % | |
|---|---|---|---|
| | | Lanthanum | Europium |
| Example 24 | Ph—P(=O)(—N(H)—C$_6$H$_4$OMe-p)—N(H)—C$_6$H$_4$OMe-p | 1.6 | 2.3 |
| Example 25 | Ph—P(=O)(—N(H)—C$_6$H$_4$Me-p)—N(H)—C$_6$H$_4$Me-p | 8.2 | 13.4 |
| Example 26 | Ph—P(=O)(—N(H)—C$_6$H$_4$Cl-p)—N(H)—C$_6$H$_4$Cl-p | 7.0 | 7.4 |
| Example 27 | Ph—P(=O)(—N(H)—C$_6$H$_4$OC$_8$H$_{17}$-p)—N(H)—C$_6$H$_4$OC$_8$H$_{17}$-p | 96.6 | 99.3 |
| Example 28 | Ph—P(=O)(—N(H)—C$_6$H$_4$C$_8$H$_{17}$-p)—N(H)—C$_6$H$_4$C$_8$H$_{17}$-p | 47.4 | 87.7 |
| Example 29 | Ph—P(=O)(—N(Me)—C$_6$H$_4$OC$_8$H$_{17}$-p)—N(Me)—C$_6$H$_4$OC$_8$H$_{17}$-p | 95.8 | 99.4 |
| Example 30 | Ph—P(=O)(—N(C$_8$H$_{17}$)—C$_6$H$_4$Me-p)—N(C$_8$H$_{17}$)—C$_6$H$_4$Me-p | 3.1 | 5.0 |
| Example 31 | Ph—P(=O)(—N(C$_8$H$_{17}$)—C$_6$H$_4$OMe-p)—N(C$_8$H$_{17}$)—C$_6$H$_4$OMe-p | 2.0 | 2.5 |
| Example 32 | C$_8$H$_{17}$—P(=O)(—N(Me)—)—N(—(CH$_2$)$_2$—) (cyclic) | 64.6 | 84.1 |
| Example 33 | Me—P(=O)(—N(Me)—)—N(—(CH$_2$)$_2$—) (cyclic) | 1.5 | 1.8 |

Example 34

To 4 mL of 1 mol/L nitric acid aqueous solution containing $1.00\times10^{-4}$ mol/L trivalent lanthanum ions and $1.00\times10^{-4}$ mol/L trivalent europium ions, 4 mL of a dichloromethane solution containing 200 μmol of the phosphonamide compound obtained in Example 8 (in the general formula [1], $R^1$=a 4-octyloxyphenyl group, $R^2$=a methyl group and two $R^3$s are united to form an ethylene group) was added, shaken for 10 minutes at 25° C. and the layer separation was carried out. The concentrations of trivalent lanthanum ions and trivalent europium ions remaining in the aqueous solution were measured by ICP emission spectrochemical analysis and the extraction ratios of trivalent lanthanum and trivalent europium ions were calculated. As a result, 94.2% (0.376 μmol) of trivalent lanthanum ions and 97.0% (0.388 μmol) of trivalent europium ions were found to be extracted from the aqueous layer to the organic layer.

Comparative Example 2

In the same manner as in Comparative example 1 except using dodecane instead of dichloromethane, the concentrations of trivalent lanthanum ions and trivalent europium ions remaining in the aqueous solution were measured by ICP emission spectrochemical analysis. As a result, all the trivalent lanthanum ions and the trivalent europium ions were found in the aqueous solution.

Examples 35 to 38

To 4 mL of 1 mol/L nitric acid aqueous solution containing $1.00\times10^{-4}$ mol/L trivalent lanthanum ions and $1.00\times10^{-4}$ mol/L trivalent europium ions, 4 mL of dodecane solution containing various concentrations of the phosphonamide compound obtained in Example 8 (in the general formula [1], $R^1$=4-octyloxyphenyl group, $R^2$=a methyl group and two R3s are united to form an ethylene group) was added and shaken for 10 minutes at 25° C. After the layer separation, the concentrations of trivalent lanthanum ions and trivalent europium ions remaining in the aqueous solution were measured by ICP emission spectrochemical analysis and the extraction ratios of trivalent lanthanum and trivalent europium ions were calculated. The results are shown in Table 2 where A denotes mmol of the phosphonamide compound.

TABLE 2

| | | Extraction ratio (%) | |
|---|---|---|---|
| | A | Lanthanum | Europium |
| Comparative example 2 | 0 | 0 | 0 |
| Example 35 | 0.2 | 94.2 | 97.0 |

TABLE 2-continued

|  | Extraction ratio (%) | | |
| --- | --- | --- | --- |
|  | A | Lanthanum | Europium |
| Example 36 | 0.1 | 40.9 | 59.1 |
| Example 37 | 0.05 | 22.8 | 35.0 |
| Example 38 | 0.02 | 6.7 | 10.2 |

Example 39

To 4 mL of 1 mol/L nitric acid aqueous solution containing $1\times10^{-4}$ mol/L trivalent lanthanum ions, $1\times10^{-4}$ mol/L trivalent cerium ions, $1\times10^{-4}$ mol/L trivalent praseodymium ions, $1\times10^{-4}$ mol/L trivalent neodymium ions, $1\times10^{-4}$ mol/L trivalent samarium ions, $1\times10^{-4}$ mol/L trivalent europium ions, $1\times10^{-4}$ mol/L trivalent gadolinium ions, $1\times10^{-4}$ mol/L trivalent terbium ions, $1\times10^{-4}$ mol/L trivalent dysprosium ions, $1\times10^{-4}$ mol/L trivalent holmium ions, $1\times10^{-4}$ mol/L trivalent erbium ions, $1\times10^{-4}$ mol/L trivalent ytterbium ions and $1\times10^{-4}$ mol/L trivalent lutetium ions, 4 mL of a dichloromethane solution containing 1 mmol of the phosphonamide compound obtained in Example 13 (in the general formula [1], $R^1$=a phenyl group, $R^2$=a methyl group and two $R^3$s are united to form an ethylene group) was added and shaken for 10 minutes at 25° C. After the layer separation, the concentration of each rare earth metal ion remaining in the aqueous solution was measured by ICP emission spectrochemical analysis and the extraction ratio of each ion was calculated. The results are shown in Table 3.

Example 40

In the same manner as in Example 39 except using dodecane instead of dichloromethane in Example 39 and using the phosphonamide compound obtained in Example 8 (in the general formula [1], $R^1$=a p-octyloxyphenyl group, $R^2$=a methyl group and two $R^3$s are united to form an ethylene group) instead of the phosphonamide compound obtained in Example 13, the extraction ratio of each ion was calculated. The results are shown in Table 3 together with the results of Example 39.

As is apparent in Table 3, in the both examples, trivalent ytterbium ions and trivalent lutetium ions could be selectively extracted.

TABLE 3

|  | Extraction ratio/% | |
| --- | --- | --- |
| Rare earth ion | Example 39 | Example 40 |
| La | 63.1 | 0.7 |
| Ce | 78.6 | 4.6 |
| Pr | 79.1 | 3.0 |
| Nd | 75.8 | 1.7 |
| Sm | 75.5 | 3.3 |
| Eu | 74.9 | 3.7 |
| Gd | 70.1 | 4.8 |
| Tb | 73.9 | 5.0 |
| Dy | 74.7 | 5.9 |
| Ho | 75.6 | 5.6 |
| Er | 77.1 | 8.9 |
| Yb | 93.2 | 27.3 |
| Lu | 95.7 | 39.4 |

Examples 41 to 44

To 12 mL of 1 mol/L nitric acid aqueous solution containing $1.00\times10^{-4}$ mol/L trivalent lanthanum ions and $1.00\times10^{-4}$ mol/L trivalent europium ions, 12 mL of a dichloromethane solution containing 3 mmol of the phosphonamide compound obtained in Example 13 (in the general formula [1], $R^1$=a phenyl group, R=a methyl group and two $R^3$s are united to form an ethylene group) was added, shaken for 10 minutes at 25° C. and the layer separation was carried out. At this time, 94.8% (1.14 μmol) of trivalent lanthanum ions and 95.3% (1.14 μmol) of trivalent europium ions were transferred from the aqueous layer to the dichloromethane layer. Then, the organic layer was divided into aliquots of 2 mL each, and 2 mL of various aqueous solutions (nitric acid aqueous solutions and acetic acid/sodium acetate aqueous solutions of various concentrations) was added thereto separately, shaken for 10 minutes at 25° C. and the layer separation was carried out. The concentrations of trivalent lanthanum ions and trivalent europium ions found in the aqueous solution were measured by ICP emission spectrochemical analysis and the back-extraction ratios were calculated. Here, back-extraction ratio indicates, when a rare earth metal ion contained in the dichloromethane layer is extracted with an aqueous layer, the ratio of the number of moles of ions transferred from the dichloromethane layer to the aqueous layer relative to the initial number of moles of ions contained in the dichloromethane layer for each ion. The back-extraction ratios of trivalent lanthanum ion and trivalent europium ion are shown in Table 4.

TABLE 4

|  |  | Back-extraction ratio/% | |
| --- | --- | --- | --- |
|  | Kind of aqueous solution | Lanthanum | Europium |
| Example 41 | 3 mol/L nitric acid aqueous solution | 98.6 | >99.9 |
| Example 42 | 1 mol/L nitric acid aqueous solution | >99.9 | >99.9 |
| Example 43 | 0.1 mol/L nitric acid aqueous solution | 99.2 | >99.9 |
| Example 44 | 0.5 mol/L acetic acid –0.5 mol/L sodium acetate aqueous solution | >99.9 | >99.9 |

INDUSTRIAL APPLICABILITY

The present invention provides a novel phosphonamide compound which is useful as an agent for extracting a rare earth metal ion or the like, a process for producing the same, and a process for extracting a rare earth metal ion from an aqueous solution containing a rare earth metal ion using the compound. By using the phosphonamide compound of the present invention as an extraction agent, a rare earth metal ion can be extremely efficiently extracted by an easy operation from an aqueous solution containing a rare earth metal ion.

Also, the rare earth metal ion extracted and transferred from an aqueous layer to an organic solvent layer by the extraction operation can be efficiently back-extracted from the organic solvent layer to an aqueous layer by mixing and contacting the organic solvent layer with a slightly acidic to acidic water different from the initial aqueous layer.

The invention claimed is:

1. A process for extracting a rare earth metal ion from an aqueous solution containing a rare earth metal ion, comprising using as an extraction agent the phosphonamide compound represented by the general formula [1]

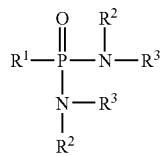

[1]

(wherein $R^1$ represents a phenyl group which may have an alkoxy group as a substituent; $R^2$ represents a hydrogen atom or a straight-chain alkyl group; $R^3$ represents a hydrogen atom or a phenyl group which may have an alkoxy group as a substituent; and the two $R^3$s may be united to form an alkylene group, a cycloalkylene group or an arylene group).

2. The extraction process according to claim 1, wherein an organic solvent is used for extraction.

3. The extraction process according to claim 2, wherein the organic solvent is not completely miscible with water.

4. The extraction process according to claim 1, wherein an aqueous solution containing a rare earth metal ion, a phosphonamide compound represented by the general formula [1] and an organic solvent which is not completely miscible with water are mixed and contacted, whereby the metal ion is transferred to the organic solvent layer.

5. A process for back-extracting a rare earth metal ion, characterized by that the organic solvent layer comprising the extracted rare earth metal ion by the extraction process according to claim 4 is mixed and contacted with a water, whereby the metal ion is transferred to the aqueous layer.

6. The back-extraction process according to claim 5, wherein the water for mixing and contacting is a weakly acidic or acidic water.

7. The extraction process according to claim 4, wherein said aqueous solution containing a rare earth metal ion has a pH value of 7 or lower.

8. The extraction process according to claim 4, wherein a volume ratio of said aqueous solution containing a rare earth metal ion to said organic solvent and phosphonamide compound is 0.001:1 to 100:1.

9. The extraction process according to claim 1, wherein the concentration of the rare earth metal ion contained in the aqueous solution is $1.0 \times 10^{-9}$ to 10 mol/L.

10. The extraction process according to claim 1, wherein the concentration of the rare earth metal ion contained in the aqueous solution is $5.0 \times 10^{-7}$ to 5.0 mol/L.

11. The extraction process according to claim 1, wherein the number of moles of the phosphonamide compound represented by the general formula [1] is 0.01 or more times the total amount of the rare earth metal ions.

* * * * *